United States Patent
Lichtenstein et al.

(10) Patent No.: US 6,723,046 B2
(45) Date of Patent: Apr. 20, 2004

(54) AT-HOME HEALTH DATA MANAGEMENT METHOD AND APPARATUS

(75) Inventors: Eric Lichtenstein, Dexter, MI (US); Vincent Cruz, Ann Arbor, MI (US); Joseph Long, Ypsilanti, MI (US); Gary Siebert, Dexter, MI (US); Charles J. Jacobus, Ann Arbor, MI (US)

(73) Assignee: Cybernet Systems Corporation, Ann Arbor, MI (US)

( * ) Notice: Subject to any disclaimer, the term of this patent is extended or adjusted under 35 U.S.C. 154(b) by 83 days.

(21) Appl. No.: 10/059,514

(22) Filed: Jan. 29, 2002

(65) Prior Publication Data

US 2003/0069751 A1 Apr. 10, 2003

Related U.S. Application Data (60) Provisional application No. 60/264,739, filed on Jan. 29, 2001.

(51) Int. Cl.[7] ................................................. A61B 5/00
(52) U.S. Cl. ...................... 600/300; 128/903; 128/904; 128/920
(58) Field of Search ................................. 600/300–301, 600/345–348, 520, 481; 128/900, 903–905, 920–921; 702/19, 22, 31–32; 705/2–4; 379/37–38, 49–50, 88.17, 93.01, 93.05–93.07, 93.28, 106.01–106.02; 482/1, 8–9; 340/573.1; 710/100; 439/488–489, 491

(56) References Cited

U.S. PATENT DOCUMENTS

| | | | | |
|---|---|---|---|---|
| 5,417,585 A | * | 5/1995 | Morin et al. | 439/488 |
| 5,633,910 A | * | 5/1997 | Cohen | 379/38 |
| 5,997,476 A | * | 12/1999 | Brown | 600/300 |
| 6,134,504 A | * | 10/2000 | Douglas et al. | 702/31 |

* cited by examiner

Primary Examiner—Max F. Hindenburg
Assistant Examiner—Michael Astorino
(74) Attorney, Agent, or Firm—Gifford, Krass, Groh, Sprinkle, Anderson & Citkowski, PC (57) ABSTRACT

A system and methodology for the acquisition of medical data from multiple, at-home patient measurement devices transfers the data via telephone communications to a remotely accessed data management and display system such as a Web-based data management system. The measurement device, which supports two-way communications between the patient and the database system, is extensible to support multiple plug-in medical devices and devices for patient input or identification. Collection of data is mediated through an interface device that is connected via a digital link (serial, network, or digital RF link) to single or multiple patient measurement devices. This interface device is connected to a network via wide area network means including standard phone lines. In the preferred embodiment, data transfer is mediated through pervasive DTMF phone networks. Although DTMF is the preferred format, alternative analog or digital audio tone formats may be used.

25 Claims, 5 Drawing Sheets

AT-HOME HEALTH DATA MANAGEMENT METHOD AND APPARATUS

REFERENCE TO RELATED APPLICATION

This application claims priority from U.S. Provisional Patent Application Ser. No. 60/264,739, filed Jan. 29, 2001, the entire contents of which are incorporated herein by reference.

FIELD OF THE INVENTION

This invention relates generally to medical data management and, in particular, to a system and methodology for the acquisition of medical data from multiple, at-home patient measurement devices, including the transfer of such data via standard telephone or wired/wireless network communications to a remotely accessed data management and display system accessible via a global computer network.

BACKGROUND OF THE INVENTION

There are numerous medical devices that afford patients the ability to take physiological measurements in the home. Patients with certain disease states, such as heart failure, diabetes, etc., are likely to own and use more than one of these medical appliances. These appliances include, home blood pressure cuffs, blood glucose monitors, and weight scales. The devices provide information such as systolic and diastolic pressure, pulse rate, blood glucose levels, and patient weight.

The consumer market and associated technologies associated with such devices have been maturing steadily for the past several years, and now many of these appliances include communication ports and software to connect them to a personal computer. As a result, there is now an opportunity to collect information from multiple home medical devices, and then present that information to both the patients and their health care providers via the World Wide Web (WWW). However, this cannot be easily carried out with current technologies for several reasons.

1. There is currently no standard for home medical appliance data and communication protocols. Individual appliances vary greatly in this respect, even appliances produced by the same manufacturer. Without a standard, it is very difficult to unify the information. A patient may have to have several different cables to connect to his or her PC to each appliance, and must run completely different software to communicate with each.

2. For many patients, there is a cost barrier to set up such a system. Many elderly and low-income patients cannot afford the purchase of a PC to download and store the information from these appliances. However, healthcare providers are beginning to recognize the potential benefit of this technology for preventative medicine that can ultimately reduce healthcare costs.

3. Even if the information is successfully gathered by the patient, it currently cannot made available to their healthcare providers in a clear, concise format.

Thus, there remains a need for an interface device to directly connect at home medical appliances to a telephone line, without a PC, for transfer to a Web-based data management system.

SUMMARY OF THE INVENTION

This invention presents a device, system, and methodology for the acquisition of data from multiple at-home patient measurement devices, and the transfer of this data via telephone or alternative digital network communications to a remotely accessed data management and display system which is preferably Web-based. Collection of data is mediated through an interface device connected via a digital link (serial, network, or digital RF link) to single or multiple patient measurement devices. For data transfer, this interface device is connected to a network via wide-area network over standard phone lines, modem or DSL.

In the preferred embodiment, the interface device automatically dials directly into a data collection server at a data management site. The data management site possesses both Database and Remote Display Server (which include Web-based) systems that provide for storage of patient records and data, and allow for access to the data by authorized users through any Web or Viewer-enabled computer. The interface device includes support for two-way communications between the patient and the database system and is extensible to support multiple plug-in medical devices and devices for patient input or identification.

Also in the preferred embodiment, data transfer is mediated through pervasive DTMF phone networks. Although DTMF is the preferred format, alternative analog or digital audio tone formats may be used. The device may therefore be equipped with auto-dialer, without necessarily requiring a full chipset modem, since the vast majority of home medical appliances are low data rate devices. In alternative embodiments, however, the connection may incorporate a modem for faster data transfer, modems for DSL, cable or RF network connections, and RF or various digital connections between the medical measurement devices and the communications device itself.

DETAILED DESCRIPTION OF THE INVENTION

Figure 1:
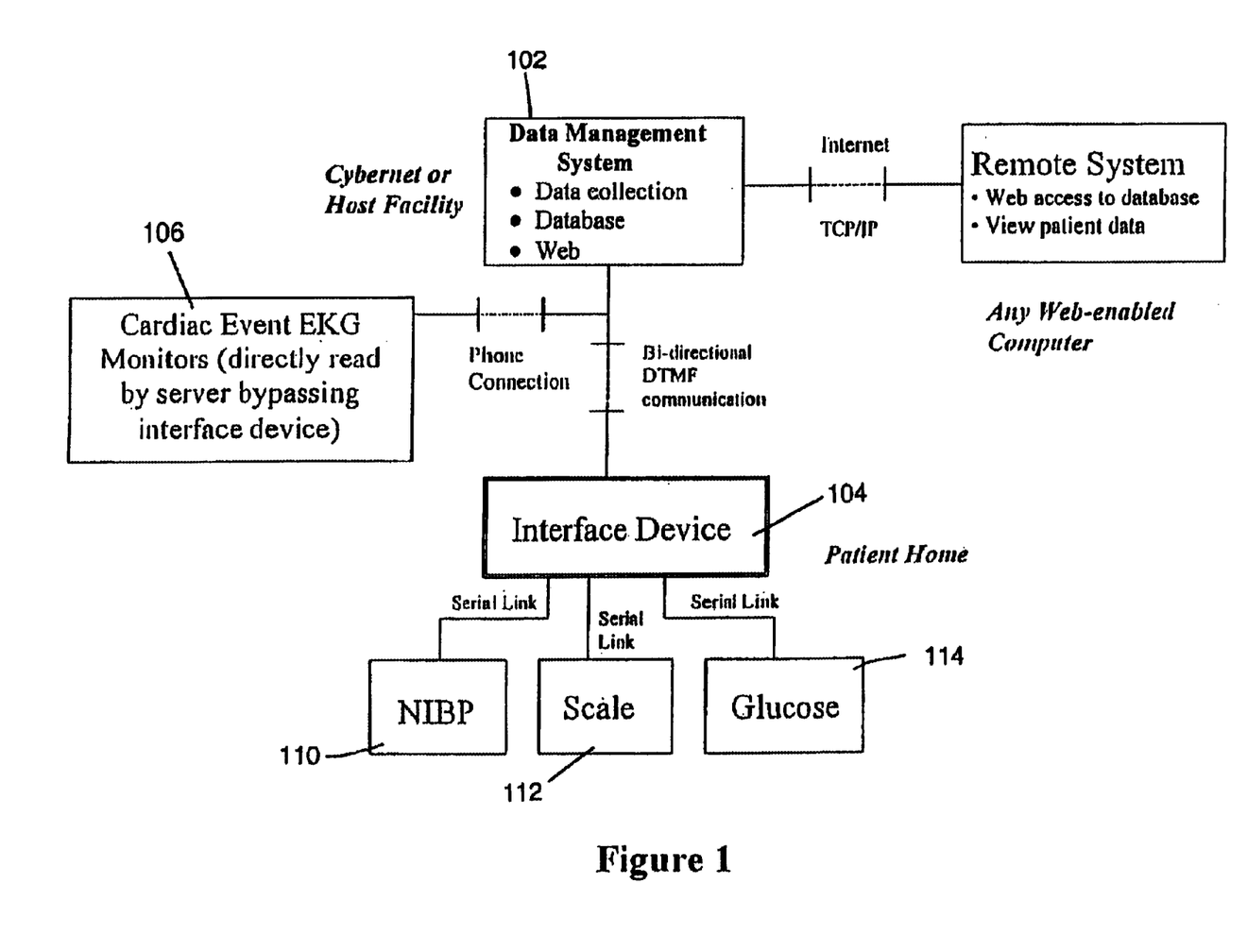
FIG. 1 illustrates an application according to the invention involving non-invasive blood pressure (NIBP), weight measurement, and glucose measurement as the patient measurements.

FIG. 1 illustrates in block-diagram form a preferred embodiment of the invention. Note that the data management system 102 can support other devices which do not require the Interface Device 104, such as EKG unit 106. In addition, different configurations can support medical measurements other than Non-Invasive Blood Pressure (NIBP) 110, Scale 112, and Glucose Measurement Unit 114.

Also, the connection between the Interface Device 104 and the Data Management System 102 can be through other means, such as DSL, cable modem, T1, RF wireless network, and the connection from the measurement units may be also through alternative digital connections such as 802.11b (RF network), USB (alternative wired digital connections), and so forth.

The following outlines the preferred requirements for the device and system operation:

- The device interface should be designed to connect to multiple low-data-rate at-home medical devices.
- The architecture should be configurable to allow for the use of different manufactures medical devices.
- The system must provide an easy-to-use interface for the patient.
- The cables that connect it to the devices should to be color-coded and/or use dissimilar connectors to prevent improper connections.
- Each Interface Device should have an electronic serial number for identification of the patient. To support multiple patients, this might include connection to a patient input or ID system.
- At least the Interface Device should be relatively small in physical size (suitable for unobtrusive desktop placement).
- Each Interface Device should have independent battery power.
- The phone interface should connect to any standard network connection supported (such as RJ-11 phone connector for phone connection).
- The system needs to operate in any time zone.
- The system should accommodate network address programming (such as prefix (or other custom) dialing requirements for phone).
- The physical packaging of the Interface Device should be durable and water resistant.
- The Interface Device should be inexpensive enough for general consumer use.
- The patient should not be required to do any configuring or programming.
- The Interface Device may incorporate a means for patient self-reporting of information through keys or other means.
- Any text displayed must be of large enough size for elderly patients viewing.
- The Interface Device should store data from the device readings until successfully transferred.
- The system should report the time and date of the data measurements.
- The system should receive the necessary regulatory approvals and meet relevant industry standards.
- Each Interface Device should be able to communicate with a remote data storage and management system.
- An effective remote viewing interface (such as Web interface) should be available for display of the measured data.

Measurement Devices

Following are three examples of at-home measurement devices that possess serial communications ports for interface to the Interface Device. Any other device, preferably with serial output, may similarly be used.

1. Non-Invasive Blood Pressure (NIBP)

| | |
|---|---|
| Manufacturer: | A&D Medical |
| Model: | UA-767PC |
| Outputs: | Systolic Pressure (mmHg) |
| | Diastolic Pressure (mmHg) |
| | Pulse Rate (per minute) |
| | Measurement Time and Date |

2. Weight Scale

| | |
|---|---|
| Manufacturer: | A&D Medical |
| Model: | UC300 |
| Outputs: | Weight (lbs. or kg. depending on specific device purchased) |

3. Glucose Measurement

| | |
|---|---|
| Manufacturer: | Lifescan |
| Model: | Surestep RS232 |
| Outputs: | Glucose (mg/dL or mmol/L, selectable) |
| | Measurement Time and Date |

The following tables summarize the characteristics of each measurement device, as relevant to performing and transferring measurements to our interface device:

| | Data requested from device? | Data pushed from device? | Remote power-up? | Start collection remotely? | Has Device ID? | Data format | Different data forms? | Has time stamp? | Serial Protocol | Baud Rate |
|---|---|---|---|---|---|---|---|---|---|---|
| NIBP | Y | N | Y | Y | Y/N[1] | ascii/hex | N | Y | RS232 | 9600 |
| Scale | N | Y | Y | Y | N | ascii | Y/N[3] | N | TTL | 2400 |
| Glucose | Y | N | N | Y[2] | Y | ascii | Y[4] | Y | TTL | 9600 |

Figure 2:
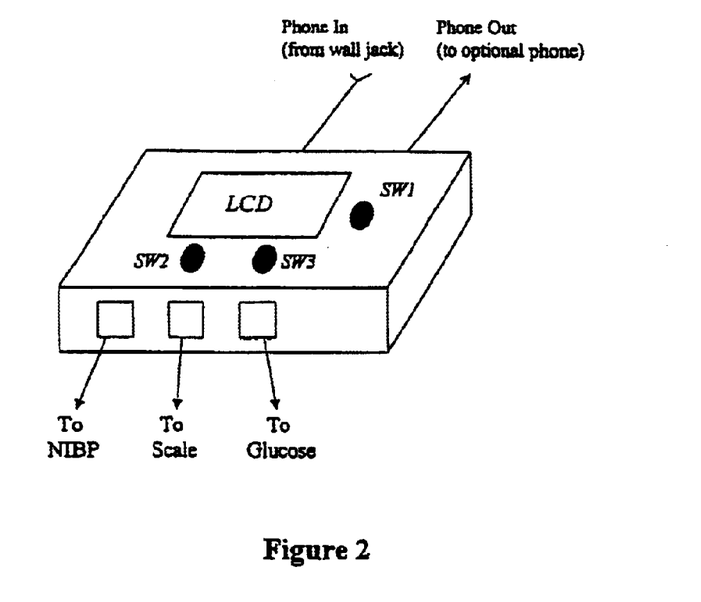
FIG. 2 illustrates an external form for the interface device.

[1]Device is not preprogrammed with ID, but an ID may be written to the device and later retrieved.
[2]Device must be already powered-up (cannot remote power-up)
[3]Two different models of the device exist: one that outputs results in pounds, the other in kilograms
[4]The device may be configured for different data and time formats, as well as glucose result in mg/dL or mmol/L The Interface Device FIG. 2 is a simplified drawing of an Interface Device according to the invention. The preferred characteristics are as follows:

| Approximate/Target Specifications: | |
|---|---|
| Size: | 2¾" × 3½" × ¾" |
| Weight: | 0.25 lbs. |
| Battery: | 2 AA |
| Power Duration: | 100–200 hours |
| LCD Display: | |
| Text: | 2 lines × 12 characters |
| Symbols: | Low battery |
| | Phone Connect |
| | Data Transfer in progress |
| | Recording Data |

Figure 3:
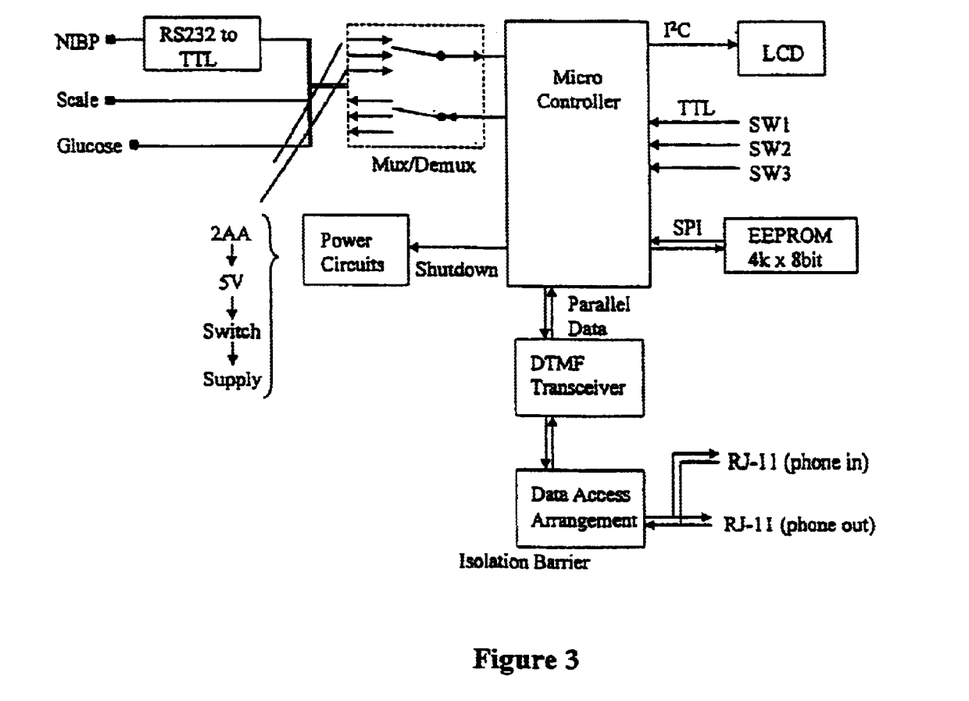
FIG. 3 is a functional block diagram for the interface device electronics.
Figure 4:
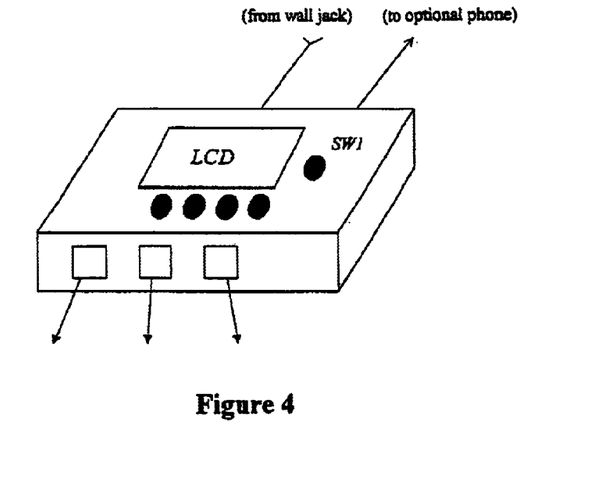
FIG. 4 depicts a unit having a larger screen and additional keys for two-way patient communications.
Figure 5:
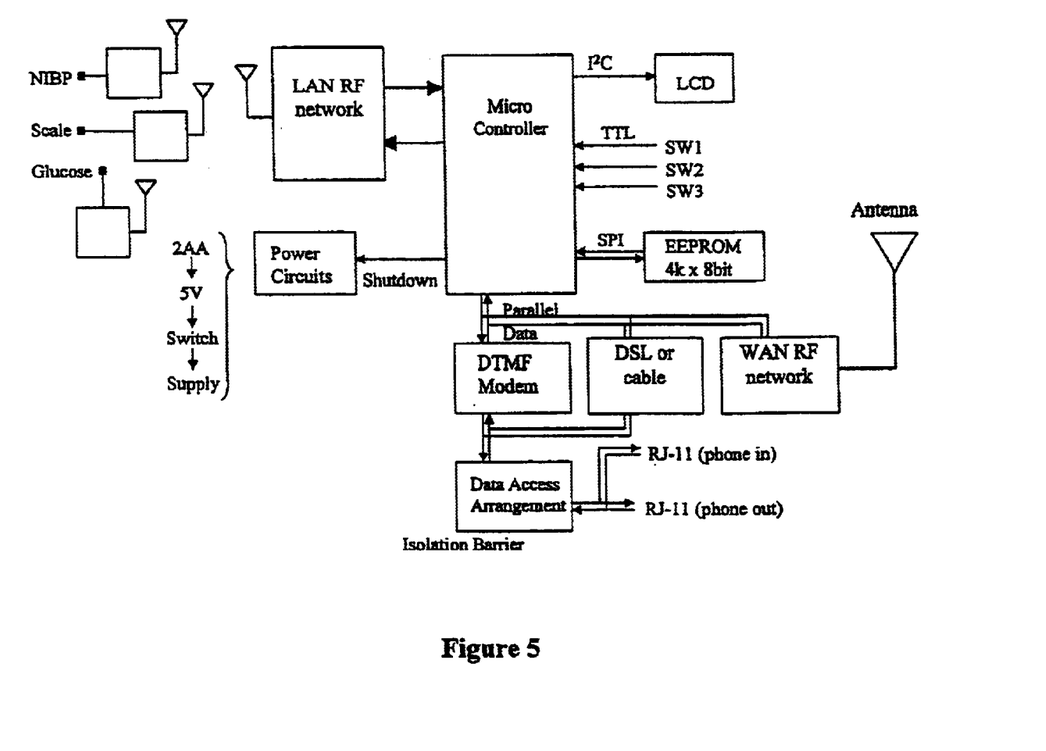
FIG. 5 shows an embodiment incorporating wireless access to measurement devices and multiple WAN network access.

Alarm/Error
Phone Interface:
Two RJ-11 connectors (for feedthrough)
Auto-dial operation
Bi-directional DTMF communication FIG. 3 is a functional block diagram depicting Interface Device electronics. In terms of alternative embodiments, FIG. 4 shows a unit that has a larger screen and additional input buttons to support two-way question and symptom reporting by the patient. FIG. 5 shows a unit that uses wireless means to communicate with each medical device and multiple means for connecting to a network that provides access to the database and web server plant.

Operational Overview

The following description outlines how the device is used by the patient and the process for measurement and transfer of data:

Patient receives devices from their healthcare provider(s) including:

One Data Interface device

One or more of: NIBP, Scale and Glucose Measurement.

The Interface Device and remain in the home with the scale device attached thereto. The Glucose and NIBP devices, on the other hand, may be disconnected from the Interface Device, with measurements being taken throughout the day in the patient's normal environment.

1. At (roughly) the same time each day, the patient connects all devices to the Cybernet device initiates the transfer process using interface buttons on the Cybernet device.
2. Directions on the Cybernet device guide the patient through the transfer process, as follows:

a. If a scale device is present, the patient steps on the scale for a measurement. The scale output is transferred to the Interface Device.

b. If a NIBP device is present, the patient may take a measurement, if desired. All stored measurements on the NIBP device are then transferred to the Interface device. Data is preferably erased on the NIBP device once successful transfer is confirmed.

c. If a glucose device is present, the patient powers up the glucose device and may take a measurement if desired. All stored measurements on the glucose device are then transferred to the Interface Device. Again, data is preferably erased on the glucose device once successful transfer is confirmed.

3. After receipt of data from each measurement device, the Interface Device automatically dials the number of the Data Management System (102 in FIG. 1).
4. If connection cannot be made, the Interface Device will wait for a predetermined period of time and then try to connect again. The device will attempt a number of times and then give up until the next day when the patient initiates transfer again.
5. Once phone connection to the Data Management System is established, the Interface Device transfers all collected data via DTMF tone communication
6. If an error occurs during transmission of the data the Interface Device will reconnect (if required) and send the data again. Methods employed to account for continued errors will include reduction of the DTMF data rate, and phone line connection.
7. Once successful transfer of the data has been confirmed, the Interface Device will delete the data and return to power-down mode.

Data Acquisition and Management Processes

Figure 6:
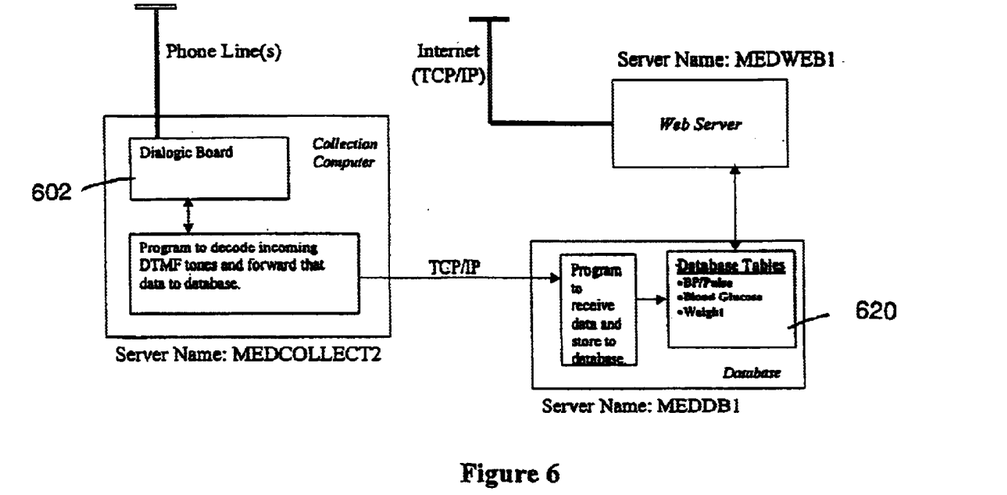
FIG. 6 illustrates a server system for acquisition and data management.

FIG. 6 presents preferred server system requirements for acquisition and management of the patient data.

Outline of the Data Collection Process:

1. Incoming phone call is received by phone interface card.
2. Phone interface card sends tone to calling system (the interface device) to let it know that we're ready to receive incoming data.
3. Data is sent via DTMF decoding of HEX values.

Two DTMF tones will represent one byte of data.
    Tone 1
       Upper 4 bits.
    Tone 2
       Lower 4 bits.
    See packet and communication descriptions that follow this outline
    Upon receipt of each packet verification of correct receipt will be done via DTMF tone back to serial-to-DTMF translation device.
       0—Check sum invalid. Resend data.
       1—Check sum verified.
4. Once data transfer has been verified the data is then decoded and sent to the database 620 where it is stored in the appropriate table based on the type of data that it is. Each device type will send data to a different table.
5. After confirmation that data has been stored in the database, a confirmation message is sent to the Interface Device which results in deletion of the data on the device

| | Packet Description: | | | |
|---|---|---|---|---|
| Disc. | Packet Version | Device Type | Data | Check Sum |
| Size$^5$ | 1 | 1 | N | 2 |

- Packet Version-1 Nibble
  ○ The first nibble sent describes the packet type to follow. It may have the following values:
    ■ 1  Version 1 data packets.
    ■ 2-F  Future Use
- Device Type-1 Nibble
  ○ This is used to describe the data type to follow. The originating device is used to determine what information is contained and how big the data packet is going to be. All packet sizes are preferably fixed.
    ■ 0  Device Information
    ■ 1  UA-767PC A&D Medical Blood Pressure Cuff
    ■ 2  Lifescan Sure Step Blood Glucose Monitor
    ■ 3  UC-300 A&D Medical Scale
    ■ 4-F  Future use by other measurement or patient ID/input devices -continued

- Data-n Bytes
  - This part of the packet contains the data that's being transferred. Its size varies with the different data types. The packet descriptions are described in further detail below.
- Check Sum-1 Byte
  - The check sum is the summation of all nibbles in the packet. It is a one byte HEX value representing the lower byte of the summation and used for error checking on the server side to verify that the entire packet was received correctly over the telephone line.

Data Packet Specifications:

| Disc. | P | T | Model Number | Serial Number | Check Sum |
|---|---|---|---|---|---|
| Size | 1 | 1 | 4 | 12 | 2 |
| Sample[6] | 1 | 0 | 0x0001 | 123456789012 | 0x32 |

- 0-Device Information
  - 8 Bytes-Hex Values
    - 4 Nibbles   Model Number (HEX)
    - 12 Nibbles  Serial Number (BCD)

| Disc. | P | T | Year | Month | Day | Hour | Min. | Sy-Di | Dia | Pulse | Check Sum |
|---|---|---|---|---|---|---|---|---|---|---|---|
| Size | 1 | 1 | 2 | 2 | 2 | 2 | 2 | 2 | 2 | 2 | 2 |
| Sample | 1 | 1 | 01 | 01 | 16 | 15 | 35 | 0x12 | 0x34 | 0x45 | 0xCC |

- 1-UA-767PC A&D Medical Blood Pressure Cuff
  - 8 Bytes-Hex Values
    - 2 Nibbles   Year              (BCD) (Years since 1900)
    - 2 Nibbles   Month             (BCD)
    - 2 Nibbles   Day               (BCD)
    - 2 Nibbles   Hour              (BCD) (24 Hour Clock)
    - 2 Nibbles   Minute            (BCD)
    - 2 Nibbles   Systolic less Diastolic   (HEX)
    - 2 Nibbles   Diastolic         (HEX)
    - 2 Nibbles   Pulse             (HEX)

| Disc. | P | T | Year | Month | Day | Hour | Min. | State | Reading | Check Sum |
|---|---|---|---|---|---|---|---|---|---|---|
| Size | 1 | 1 | 2 | 2 | 2 | 2 | 2 | 1 | 3 | 2 |
| Sample | 1 | 2 | 01 | 01 | 16 | 15 | 35 | 0000b | 500 | 0xCC |

- 2-Lifescan Sure Step Blood Glucose Monitor
  - 7 Bytes-
    - 2 Nibble   Year       (BCD) (2 digit value)
    - 2 Nibble   Month      (BCD)
    - 2 Nibble   Day        (BCD)
    - 2 Nibble   Hour       (BCD)
    - 2 Nibble   Minute     (BCD)
    - 1 Nibble   State      (BIT)
      - Bit 3-Calibration       (1-Yes, 0-No)
      - Bit 2-Error             (1-Yes, 0-No)
      - Bit 1-Check sum error   (1-Yes, 0-No)
      - Bit 0-HIGH              (1-Yes, 0-No)
    - 3 Nibble   Reading    (HEX)

| Disc. | P | T | Year | Month | Day | Hour | Min. | Param | Weight | Check Sum |
|---|---|---|---|---|---|---|---|---|---|---|
| Size | 1 | 1 | 2 | 2 | 2 | 2 | 2 | 1 | 5 | 2 |
| Sample | 1 | 3 | 01 | 01 | 16 | 15 | 35 | 0000b | 01250 | 0xCC |

- 3-UC-300 A&D Medical Scale
  - 8 Bytes-
    - 2 Nibble   Year       (BCD) (2 digit value)
    - 2 Nibble   Month      (BCD)
    - 2 Nibble   Day        (BCD)
    - 2 Nibble   Hour       (BCD)
    - 2 Nibble   Minute     (BCD)
    - 1 Nibble   Reading Parameters
      - Bit 3-Future Use
      - Bit 2-Weight Type      (1-OL, 0-ST)
      - Bit 1-Sign of Reading  (1-"−", 0-"+")
      - Bit 0-Weight Unit      (1-kg, 0-lb)
    - 5 Nibbles  Weight Value   (BCD)

[5]Sizes = Number of Nibbles (4 bits)
[6]Samples have the following format. #-BGD, 0xXX-Hex value, XXXXb-Binary nibble Communication Specifications:
DTMF Tones Conversion Chart for Incoming Server Messages

| PIC Register Value | | | | Incoming Tone | Actual Value |
|---|---|---|---|---|---|
| 0 | 0 | 0 | 0 | D | 0 |
| 0 | 0 | 0 | 1 | 1 | 1 |
| 0 | 0 | 1 | 0 | 2 | 2 |
| 0 | 0 | 1 | 1 | 3 | 3 |
| 0 | 1 | 0 | 0 | 4 | 4 |
| 0 | 1 | 0 | 1 | 5 | 5 |
| 0 | 1 | 1 | 0 | 6 | 6 |
| 0 | 1 | 1 | 1 | 7 | 7 |
| 1 | 0 | 0 | 0 | 8 | 8 |
| 1 | 0 | 0 | 1 | 9 | 9 |
| 1 | 0 | 1 | 0 | 0 | A |
| 1 | 0 | 1 | 1 | * | B |
| 1 | 1 | 0 | 0 | # | C |
| 1 | 1 | 0 | 1 | A | D |
| 1 | 1 | 1 | 0 | B | E |
| 1 | 1 | 1 | 1 | C | F |

Server Handshaking Protocols—
½ second wait after each response before device starts continues.
Ready to Receive—"AB"
Packet ACK (Acknowledge)—"AB"
Packet NACK (No Acknowledge—Error checksum etc.)—"CD"

After initial connection Client waits up to 3 sec for server to send Ready to Receive. Client then sends a Device Information Packet. Waits 1 second for Packet ACK or NACK. If no ACK or NACK then client hangs up and tries dials again. If ACK received client begins sending data packets. If NACK client sends Device Information Packet again. If NACK again client increases inter digit delay and retransmits Device Information Packet. Continue to increase inter-digit delay until ACK or max delay limit is reached.

Estimate of Data Transfer Time (Phone DTMF Messaging):
Data Collection Assumptions:
1 NIBP reading per day
1 Scale reading per day
5 glucose readings per day
Data is preferably transferred once per day
Approximate Data Sizes (# of ASCII Words) for Each Data Component:

| Header: | 10 = | 10 words |
|---|---|---|
| NIBP: | 10 = | 10 words |
| Scale: | 10 = | 10 words |
| Glucose: | 7/reading + 2 = | 45 words |
| Words to be transferred for acquired data = | | 75 words |

Given DTMF Transfer rate=200 mSec for Each Word:

= 15 seconds for data
+ 5 seconds for handshaking responses (Five 1-second responses)
⇒ 20 seconds total transfer time

*excludes dialing and connection time, and assumes no errors/retry

Other Transmission Interfaces

Communications through other digital transmission interfaces like DSL, wireless network, or Ethernet will code data packets in format comparable to those described in the last section; however, the packet transmission means used for Internet-compatible networks includes its own packet timing, sequencing, and acknowledgement procedures which are documented in the various RFIs describing Internet and Internet protocol operations.

Database Requirements

Figure 7:
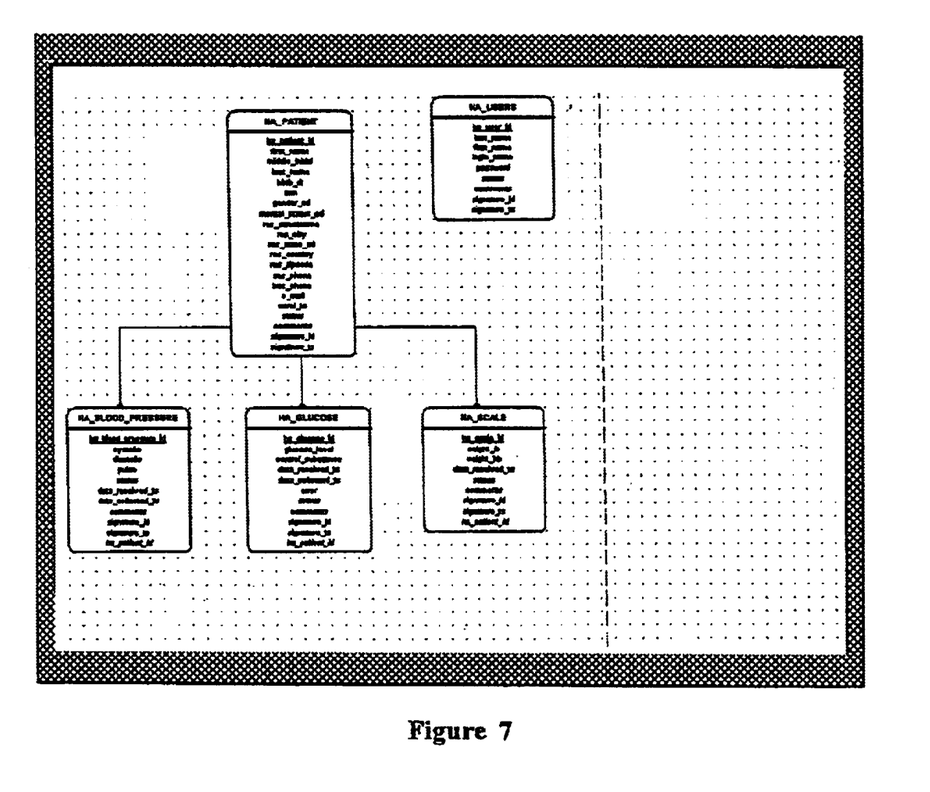
FIG. 7 illustrates a database model of new tables required.

Initially an existing SQL database will be implemented along with additional tables to manage the data from the new device. FIG. 7 presents additional tables that may be required. Storage means through flat files or other databases is an alternative.

Web Interface

Figure 8:
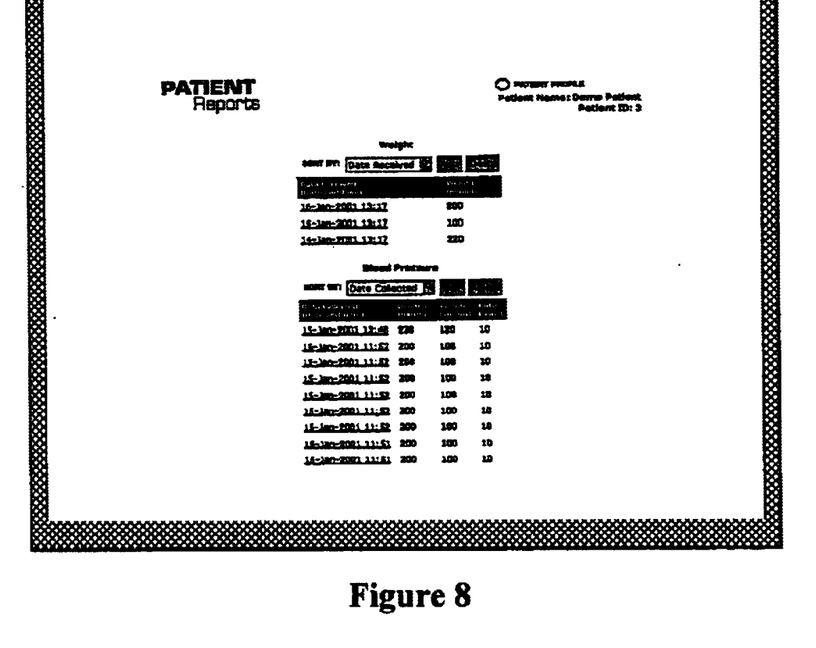
FIG. 8 illustrates a web interface full report.
Figure 9:
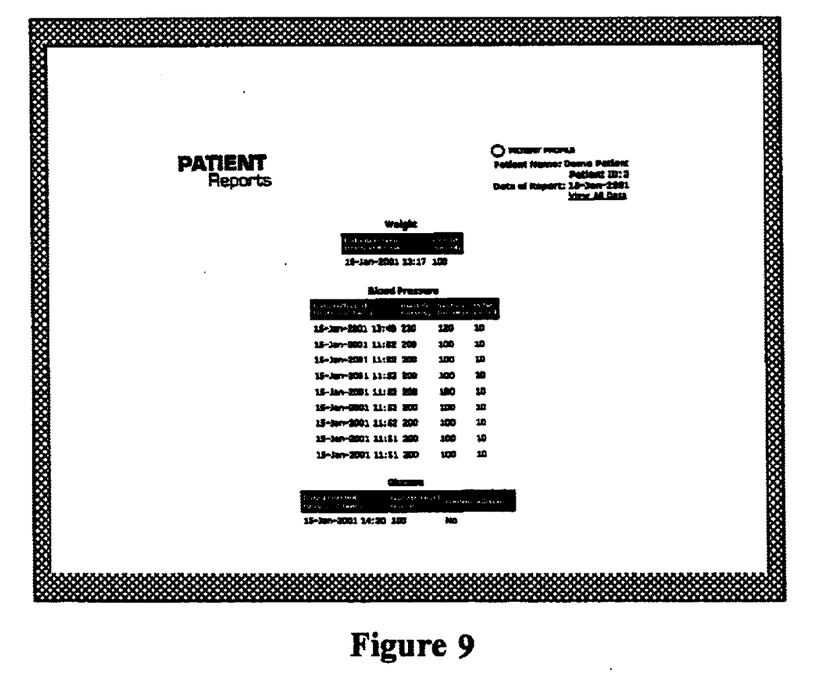
FIG. 9 illustrates a web interface daily report.

In the preferred embodiment, a simple web interface has been developed that allows a user to logon and view all data (NIBP, weight, and glucose) that has been transferred from the interface device. Viewing systems which provide remote access to the data but which are not strictly connectionless or Web-based can be alternative implementations. FIGS. 8 and 9 illustrate the envisioned form for these pages.

We claim:

1. A medical data collection and management system, comprising:
   a) one or more physiological measurement units, each outputting medical data;
   b) an electronic interface device, including:
      one or more inputs, each operative to receive medical data from a respective one of the physiological measurement units, and
      an interface for transferring the medical data over a telephone or digital network;
   c) a data management system, including:
      an input for receiving the medical data from the electronic interface device,
      a database for storing the medical data, and
      an interface enabling the medical data to be viewed over a wide-area network; and
   d) a physiological monitor operative to collect and route medical data directly to the data management system, effectively bypassing the electronic interface device.

2. The medical data collection and management system of claim 1, wherein the medical data is transferred via a dual-tone, multi-frequency (DTMF) format.

3. The medical data collection and management system of claim 1, wherein the digital network, the wide-area network, or both, comprise the Internet.

4. The medical data collection and management system of claim 1, including physiological measurement units associated with one or more of the following:
   non-invasive blood pressure (NIBP),
   weight measurement, and
   glucose measurement.

5. The medical data collection and management system of claim 1, wherein the medical data are accessed from the database using an Internet protocol.

6. The medical data collection and management system of claim 1, wherein at least the electronic interface device is a portable unit adapted for in-home use.

7. The medical data collection and management system of claim 1, further including a wireless interface between the electronic interface device and the telephone or digital network.

8. The medical data collection and management system of claim 1, further including a wireless interface between at least one of the physiological measurement units and the electronic interface device.

9. The medical data collection and management system of claim 1, further including a color-coded or physically different hardwired interface between at least one of the physiological measurement units and the electronic interface device to prevent misconnection.

10. A method of gathering and managing medical data, comprising the steps of:
   receiving medical data at an electronic interface device from one or more physiological measurement units;
   transferring the medical data to a data management system over a telephone or digital network
   formatting the data at the data management system for viewing over a wide-area network; and
   collecting and routing the medical data directly to the data management system, thereby bypassing the electronic interface device.

11. The method of claim 10, wherein the step of transferring the medical data includes the use of a dual-tone, multi-frequency format.

12. The method of claim 10, wherein the digital network, the wide-area network, or both, comprise the Internet.

13. The method of claim 10, wherein the medical data includes one or more of the following:
   non-invasive blood pressure (NIBP),
   weight measurement, and
   glucose measurement.

14. The method of claim 10, further including the step of storing the medical data in a database which is accessed for viewing.

15. The method of claim 10, wherein the medical data bypassing the electronic interface device comprises EKG data.

16. The method of claim 10, wherein the medical data bypassing the electronic interface device originates from a medical practice, laboratory, or hospital.

17. A medical data collection and management system, comprising:
   a) a plurality of physiological measurement units, each outputting a different form of medical data;
   b) a plurality of portable, electronic interface devices, each adapted for in-home use, each device including:
      a plurality of inputs, each operative to receive medical data from a respective one of the physiological measurement units, and
      an interface for communicating the medical data in audio tone form over a standard telephone network;
   c) a data management system, including:
      an input for receiving the audio tones from the various electronic interface devices,
      a database for storing the medical data received from the electronic interface devices,
      an interface enabling the medical data to be viewed over a wide-area network; and
   d) one or more physiological monitors operative to collect and route medical data directly to the data management system, bypassing the electronic interface device.

18. The medical data collection and management system of claim 17, wherein the audio tones generated by the interface devices conform to a dual-tone, multi-frequency (DTMF) format.

19. The medical data collection and management system of claim 17, wherein the wide-area network is the Internet.

20. The medical data collection and management system of claim 17, including physiological measurement units associated with one or more of the following:
   non-invasive blood pressure (NIBP),
   weight measurement, and
   glucose measurement.

21. The medical data collection and management system of claim 17, wherein the medical data are stored in the database using an Internet protocol.

22. The medical data collection and management system of claim 17, wherein at least the electronic interface device is a portable unit adapted for in-home use.

23. The medical data collection and management system of claim 18, further including a wireless interface between the electronic interface device and the standard telephone network.

24. The medical data collection and management system of claim 18, further including a wireless interface between at least one of the physiological measurement units and the electronic interface device.

25. The medical data collection and management system of claim 18, further including a color-coded or physically different hardwired interface between at least one of the physiological measurement units and the electronic interface device to prevent misconnection.

* * * * *